United States Patent
Davis et al.

(10) Patent No.: US 10,144,017 B2
(45) Date of Patent: Dec. 4, 2018

(54) CENTRIFUGAL MIXING SPRAY NOZZLE

(71) Applicant: NEOMEND, INC., Irvine, CA (US)

(72) Inventors: Peter G. Davis, Dana Point, CA (US); Tina L. McArthur, Fallbrook, CA (US); Andrew J. Basilio, Walnut, CA (US); Kristina L. Clampitt, Costa Mesa, CA (US)

(73) Assignee: Neomend, Inc., Irvine, CA (US)

( * ) Notice: Subject to any disclaimer, the term of this patent is extended or adjusted under 35 U.S.C. 154(b) by 0 days.

(21) Appl. No.: 14/213,162

(22) Filed: Mar. 14, 2014

(65) Prior Publication Data

US 2014/0263749 A1    Sep. 18, 2014

Related U.S. Application Data

(60) Provisional application No. 61/788,311, filed on Mar. 15, 2013.

(51) Int. Cl.
   *B05B 1/34*    (2006.01)
   *B01F 5/00*    (2006.01)
   (Continued)

(52) U.S. Cl.
   CPC .......... *B05B 1/3478* (2013.01); *B01F 5/0057* (2013.01); *B01F 13/0023* (2013.01);
   (Continued)

(58) Field of Classification Search
   CPC . A61B 17/00491; A61M 5/19; A61M 5/3007; B05B 1/3415; B05B 1/3431;
   (Continued)

(56) References Cited

U.S. PATENT DOCUMENTS 4,260,110 A * 4/1981 Werding ............... B05B 1/3436
                                                        239/404
4,923,448 A * 5/1990 Ennis, III ................ A61M 5/31
                                                        128/200.14
(Continued)

FOREIGN PATENT DOCUMENTS

EP          2163204 A1     3/2010
JP       2009-537291 A    10/2009
(Continued)

OTHER PUBLICATIONS

International Search Report dated Jul. 9, 2014 for corresponding PCT Application No. PCT/US2014/028783.
(Continued)

*Primary Examiner* — Alexander Valvis
*Assistant Examiner* — Cody Lieuwen
(74) *Attorney, Agent, or Firm* — Wolf, Greenfield & Sacks, P.C.

(57) ABSTRACT

A nozzle tip assembly comprises a nozzle housing and a break-up insert. The nozzle assembly is adapted for receiving multiple pre-cursor fluids from multiple lumen. The pre-cursor fluids are kept substantially separate and forced around the break-up insert into a channel formed between the insert and the nozzle housing. Fluid is forced into fluted channels on a distal end of the break-up insert into a swirl chamber where mixing occurs prior to being expelled through an exit orifice in the nozzle housing.

9 Claims, 6 Drawing Sheets

Figure 3:
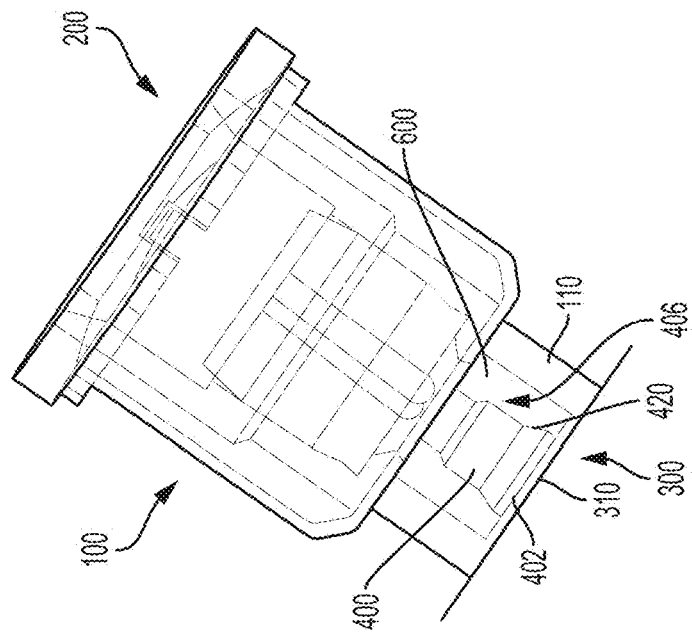

(51) Int. Cl.
  *B01F 13/00* (2006.01)
  *B01F 15/02* (2006.01)
  *A61B 17/00* (2006.01)

(52) U.S. Cl.
  CPC ........ *B01F 15/0226* (2013.01); *B05B 1/3415* (2013.01); *B05B 1/3431* (2013.01); *B05B 1/3436* (2013.01); *A61B 2017/00495* (2013.01)

(58) Field of Classification Search
  CPC ... B05B 1/3463; B05B 1/3478; B05B 1/3436; B01F 5/0057; B01F 13/0023; B01F 15/0226
  USPC ....... 239/399, 403, 428, 432, 474, 492, 400; 604/82–92, 191; 606/213, 214; 222/137
  See application file for complete search history.

(56) References Cited

U.S. PATENT DOCUMENTS

| | | | | |
|---|---|---|---|---|
| 5,116,315 | A * | 5/1992 | Capozzi | A61B 17/00491 222/137 |
| 5,605,255 | A * | 2/1997 | Reidel | A61B 17/00491 222/137 |
| 6,517,012 | B1 | 2/2003 | Slowik et al. | |
| 2003/0069537 | A1 * | 4/2003 | Spero | A61B 17/00491 604/82 |
| 2008/0067265 | A1 | 5/2008 | Songbe et al. | |
| 2009/0230214 | A1 | 9/2009 | Keller | |
| 2010/0065660 | A1 * | 3/2010 | Hull | A61B 17/00491 239/428 |
| 2010/0096481 | A1 * | 4/2010 | Hull | A61B 17/00491 239/600 |
| 2010/0114158 | A1 * | 5/2010 | Hattan | A61B 17/00491 606/214 |
| 2011/0319930 | A1 * | 12/2011 | Roush | A61B 17/00491 606/213 |

FOREIGN PATENT DOCUMENTS

| | | |
|---|---|---|
| JP | 2010-148855 A | 7/2010 |
| JP | 2011-083615 A | 4/2011 |
| WO | WO 2007/131371 A1 | 11/2007 |
| WO | WO 2011/127045 A2 | 10/2011 |

OTHER PUBLICATIONS

Supplemental European Search Report for EP14763389 dated Sep. 9, 2016.

* cited by examiner

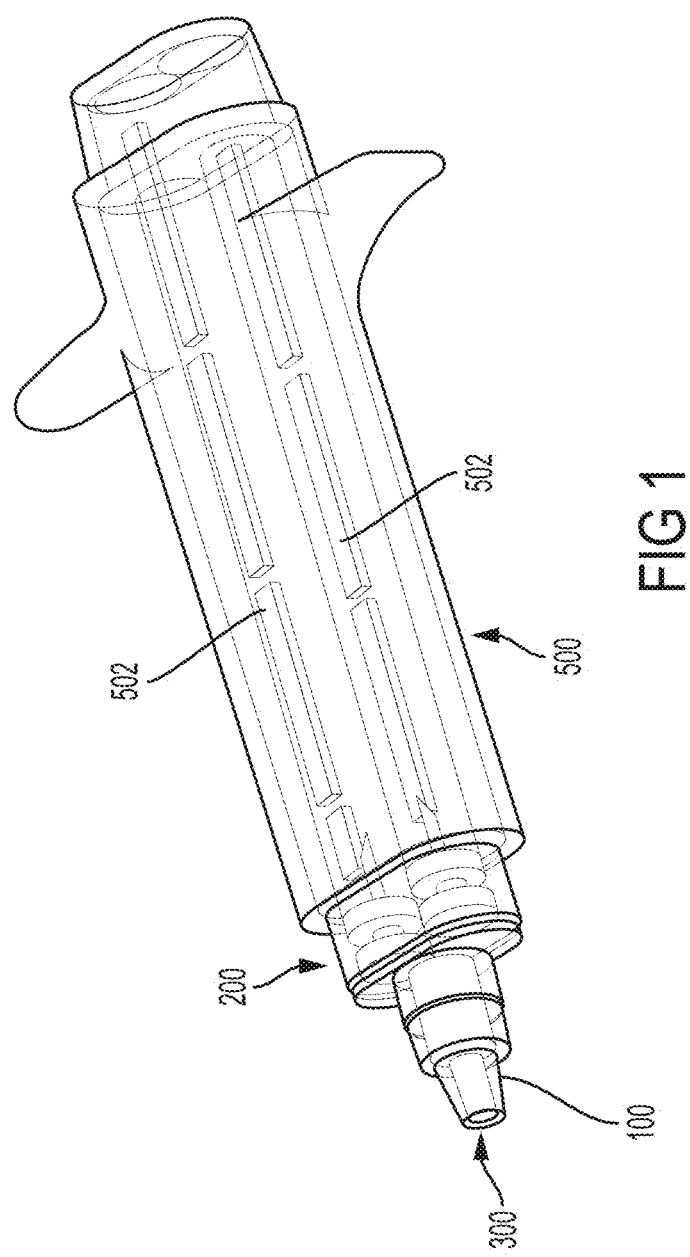

CENTRIFUGAL MIXING SPRAY NOZZLE

CROSS-REFERENCE TO RELATED APPLICATIONS

This application claims priority to U.S. Provisional Patent Application No. 61/788,311, filed Mar. 15, 2013, which is incorporated herein by reference in its entirety.

BACKGROUND OF THE INVENTION

The application of multi-component sealants and other multi-component fluid products requires the effective mixing of multiple fluids. In the case of medical sealants, proper mixing is required so that when the multi-component sealant reaches a targeted tissue, vessel or organ the pre-cursors components are mixed, allowing cross-linking, tissue reaction, adherence, and/or curing occur.

Several ways of achieving such mixing have been previously developed, including a mixing tip that requires a 'static mixer' that works to 'turn' the fluids through a complex geometric baffle to achieve mixing. The extended length of the static mixer limits its function with fast setting chemistries as the tip often becomes blocked as sealant sets before exiting an orifice for spraying or within an unacceptable interval limiting its potential commercial opportunity.

As such, there is a need for improved multi-component mixing and delivery nozzles.

SUMMARY

Some embodiments provide a nozzle tip assembly for mixing multiple pre-cursor fluids, the nozzle tip assembly comprising a nozzle housing, itself comprising a proximal end adapted for receiving a delivery portion of a multi-lumen dispenser, a distal end defining an exit orifice, and a sidewall extending from proximal end to distal end; and a break-up insert, itself comprising a proximal end, a distal end, further defining at least three fluted channels and a central, recessed swirl chamber and a sidewall extending between the proximal end and distal end; wherein the sidewall of the break-up insert and the sidewall of the nozzle housing define a channel therebetween for fluid communication between the lumen and the at least three fluted channels.

In some embodiments, the swirl chamber is defined by a substantially centrally located semi-spherical recess in the distal end of the break-up insert.

In some embodiments, each of the fluted channels approaches the swirl chamber at an angle to facilitate mixing of the pre-cursor fluids in the swirl chamber.

In some embodiments, the distance between the sidewall of the break-up insert and the nozzle housing sidewall decreases from proximal end to distal end.

In some embodiments, the break-up insert comprises one or more sloped shoulders to decrease the distance between the sidewall of the break-up insert and the nozzle housing sidewall.

In some embodiments, the at least three fluted channels are equidistant from one another.

In some embodiments, the nozzle housing is adapted for coupling to a dual barrel syringe.

In some embodiments, the nozzle housing is adapted for coupling to a dual lumen delivery device.

In some embodiments, the nozzle housing is adapted for coupling to a tri-lumen delivery device.

Some embodiments provide a multi-component delivery device comprising a multi-lumen delivery device; and a nozzle tip assembly comprising a nozzle housing, itself comprising a proximal end adapted for receiving a delivery portion of a multi-lumen dispenser, a distal end defining an exit orifice, and a sidewall extending from proximal end to distal end; and a break-up insert, itself comprising a proximal end, a distal end, further defining at least three fluted channels and a central, recessed swirl chamber and a sidewall extending between the proximal end and distal end; wherein the sidewall of the break-up insert and the sidewall of the nozzle housing define a channel therebetween for fluid communication between the lumen and the at least three fluted channels; wherein the sidewall of the break-up insert and the sidewall of the nozzle housing define a channel therebetween for fluid communication between the lumen and the at least three fluted channels; wherein the nozzle assembly is coupled to the multi-lumen delivery device such that each of the lumen is in fluid communication with the swirl chamber and exit orifice via the fluted channel and the channel between the nozzle housing and break-up insert sidewall.

BRIEF DESCRIPTION OF THE DRAWINGS

FIG. 1 is a perspective view of an exemplary dual syringe have a nozzle tip assembly in accordance with some embodiments.

FIG. 2 is a perspective cross-section rendering of a nozzle tip assembly in accordance with some embodiments.

FIG. 3 is a schematic cross-section of the embodiment of FIG. 2.

FIG. 4 is a distal end view of a break-up insert in accordance with some embodiments.

FIG. 5 is a perspective view of a break-up insert with baffles in accordance with some embodiments.

FIG. 6 depicts a distal end view of another embodiment of a break-up insert in accordance with some embodiments.

FIG. 7 depicts a perspective view of another embodiment of a break-up insert in accordance with some embodiments.

FIG. 8 depicts a distal end view of another embodiment of a break-up insert in accordance with some embodiments.

FIG. 9 depicts a perspective view of another embodiment of a break-up insert in accordance with some embodiments.

FIG. 10 depicts a side view of a break-up insert with baffles in accordance with some embodiments disclosed herein.

FIG. 11 depicts a distal end view of another embodiment of a break-up insert in accordance with some embodiments.

FIG. 12 depicts a perspective view of another embodiment of a break-up insert in accordance with some embodiments.

The drawings, including any dimensions recited therein are provided for illustrative purposes only. They are not meant to be limiting in any way.

DETAILED DESCRIPTION OF THE INVENTION

Described herein is a centrifugal mixing nozzle tip capable of mixing a multi-component fluid product, such as a sealant. In some embodiments, this is accomplished without the aid of any propellants allowing user controlled spray techniques. The nozzle design is efficient and limits tip clogging. In some embodiments, the nozzle features are adaptable to viscosity mis-match and/or molecular weight differences between the component pre-cursor fluids.

As used herein, multi-component product or system refers to a mixed product resulting from two or more pre-cursor components. Exemplary multi-component systems include medical sealants, glues, and epoxies, in and out of the medical setting.

The centrifugal mixing nozzle will be described herein with reference to a two-component medical sealant, particularly a sealant comprising a biological component and polymeric component, although the disclosed tips are not limited to two-component systems or this particular sealant.

The pre-cursor components may be selected for the desired properties and any multi-component system may be used. For examples, the biologic material (preferably albumin and PEG) in a medical sealant may be tunable based on protein fragments that affect elongation, adhesiveness, gelation time, % swelling, degradation rate, pH, sterilization efficiency, Young's modulus, ultimate tensile strength, durometer, viscosity, tertiary cross-linking and others.

Generally, a nozzle tip assembly 100 for mixing multiple pre-cursor fluids (502, 504) comprises a nozzle housing, itself comprising a proximal end 200 adapted for receiving a delivery portion of a multi-lumen dispenser 500, a distal end 300 defining an exit orifice 310, and a sidewall 110 extending from proximal end to distal end; and a break-up insert 400, itself comprising a proximal end, a distal end further defining at least three fluted channels 402 and a central, recessed swirl chamber 404, and a sidewall 406 extending between the proximal end and distal end; wherein the sidewall 406 of the break-up insert 400 and the sidewall 110 of the nozzle housing define a channel 600 therebetween for fluid communication between the lumen and the at least three fluted channels 402.

In some embodiments, the swirl chamber 404 is defined by a substantially centrally located semi-spherical recess in the distal end of the break-up insert. By semi-spherical it is meant that the base is circular and the recess essentially domed, a true semi-sphere is not required. Additionally, any geometric shape may be used. While it is contemplated that a semi-spherical shape enhances the swirling and mixing effect, mixing could also be facilitated by turbulence created in a swirl chamber having a straight side, such as a square or rectangle, or a cylindrical or cone shape may also be used. The applied force which drives the multi-component fluids into the swirl chamber also forces mixed material out through the exit orifice which is substantially aligned centrally with respect to the swirl chamber.

In some embodiments, each of the fluted channels approaches 402 the swirl chamber 404 at an angle to facilitate mixing of the pre-cursor fluids in the swirl chamber. (The swirl chamber is denoted with dotted lines for illustrative purposes in FIG. 4.) In a semi-spherical embodiment, this angle is somewhere between a direct radius and a tangent to the swirl chamber. Although a radial approach is possible, it is believed an offset approach enhances swirling and, therefore, mixing. The fluted channels 402 may take any suitable cross-sectional shape, from relatively flat to semi-circular. The size and shape should be such that the fluid velocity does not decrease from that attained in the channel 600 between the nozzle housing and break-up insert 400.

In some embodiments, the distance between the sidewall 406 of the break-up insert 400 and the nozzle housing sidewall 110 decreases from proximal end 200 to distal end 300. As depicted, the break-up insert 400 comprises one or more sloped shoulders 420 to decrease the distance between the sidewall of the break-up insert and the nozzle housing sidewall, a smoother transition may also be employed. The gradual reduction increases back pressure and increases fluid velocity as the components approach the swirl chamber.

In some embodiments, the at least three fluted channels 402 are equidistant from one another. In a three fluted design, the fluted channels are approximately 120 degrees from one another. In theory, two fluted channels could be used, but three fluted channels are believed to achieve more even mixing and better flow characteristics.

As should be appreciated, the nozzle tip assembly can be coupled to a multi-component delivery device comprising a multi-lumen delivery device. Although it is contemplated that the nozzle tip assembly can be easily removed and replaced, for example during a surgical procedure, without having to replace the entire product delivery device, it is possible that the nozzle tip assembly could be permanently affixed to a single use device.

The nozzle tip assembly is configured to accept fluid with multiple discrete pathways from a manually operated applicator system capable of transmitting force to accelerate fluid from still to a high velocity. The fluids enter into the nozzle tip where flow continues toward the break-up insert which may have upper baffles 450 but has effectively blocked the central pathway having only small channels 460 along the outer wall which accelerates fluids while providing resistance to the applicator. These fluids continue along the channel between the break-up insert and the nozzle wall until nearly reaching an exit orifice at the distal end of the nozzle. Just proximal of the housing wall of the nozzle distal end exit orifice, the channels direct the fluid into substantially radial fluted channels on the distal end of the break-up insert into a common zone referenced here as the swirl chamber. In some embodiments, there are at least three fluted channels. The swirl chamber is a general semi-spherical carve out substantially at the center of the distal end of the break-up insert. The heretofore substantially unmixed pre-cursor components meet in the swirl chamber and are forced together in a swirling manner due to the angles in which they enter the swirl chamber via the fluted channels. The depth of the swirl chamber is designed for each set of chemistry formulations to enable proper mixing. The center of the swirl chamber is aligned with the exit orifice, which typically is smaller than the swirl chamber, at the tip of the nozzle housing. The shape and size (diameter or slot or other geometry) of the exit orifice affects the spray pattern desired by the user while providing counter resistance to the applicator.

FIG. 1 shows an exemplary multi-component delivery syringe. In this instance, a two-component system is shown. Notably, each pre-cursor component is separately housed and can be pushed toward the distal nozzle end via a plunger. Mixing occurs in the mixing nozzle as described above, before the mixed multi-component product exits the exit orifice.

Figure 2:
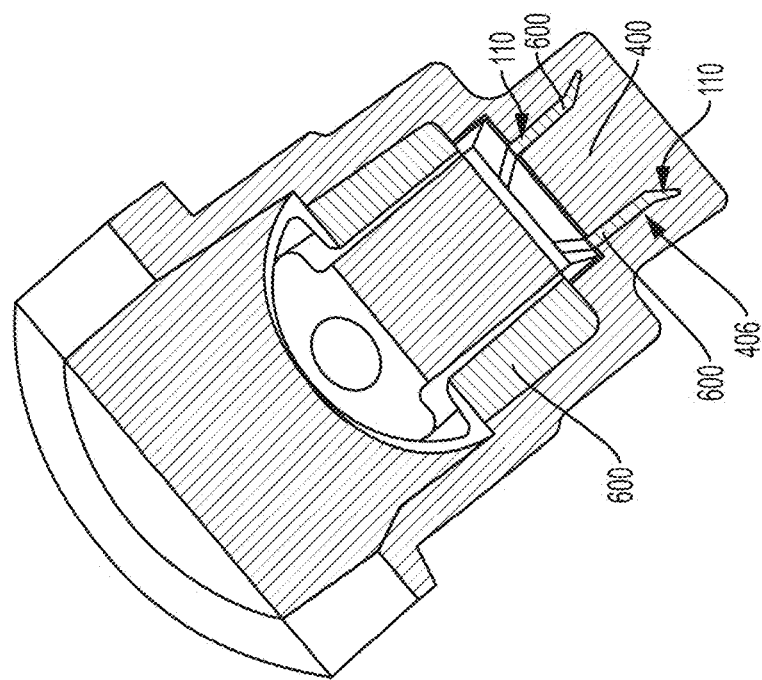
Figure 4:
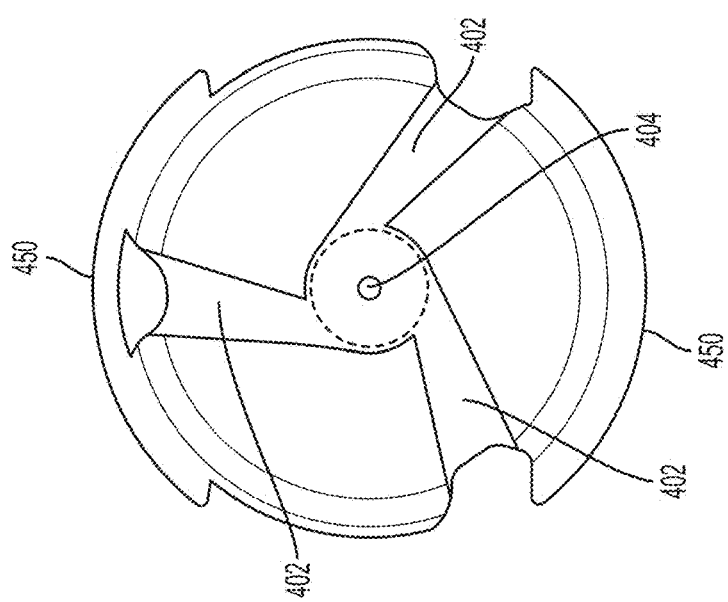

FIGS. 2 and 3 show cross-sectional views of an exemplary nozzle tip. A nozzle housing is provided for coupling to the dispenser at a proximal end. As depicted, a silicone seal is provided to secure the dispenser to the housing such that, if necessary, the tip may be removed and replaced. The nozzle may also include a dedicated lumen section for delivering the pre-cursor components separately to the break-up insert. The break-up insert fits within the walls of the nozzle housing together defining an outer channel therebetween. In some embodiments, as shown, the channel narrows as it approaches the distal end of the nozzle. This allows for buildup of back pressure and increases fluid acceleration. The distal end wall of the nozzle housing defines a centrally located exit orifice. FIG. 4 shows an exemplary end wall of the break-up insert 400. The end wall defines at least three fluted channels 402 directing fluids to the swirl chamber 404 which is generally a semi-spherical cut-out in the distal end of the break-up insert 400. The swirl chamber 404 can have other shapes, but the semi-spherical shape fits well with the swirling action created. The fluted chambers 402, as shown, are preferably equidistant from one another and enter the swirl chamber 404 at an angle rather than from a purely radial direction. The offset nature is believed to aid in creating the swirling mixing pattern.

This design allows for minimal mixing of the pre-cursor components prior to reaching the fluted channels or swirl chamber, thus minimizing the likelihood that the pre-cursor components will mix and cure in the nozzle. This allows for extended use without fear of clogging between applications during the same procedure. Simply wiping the tip of the nozzle is sufficient in most cases to prevent clogging of the tip. This, for example, allows a surgeon to apply sealant, review the surgical site, and re-apply if necessary, without replacing the nozzle in most instances.

In some embodiments, the fluted channels 402 are approximately 120° from each other. In some embodiments, the fluted channels 402 narrow as they approach the swirl chamber, thus building pressure and fluid acceleration. As will be appreciated, the corners of the entry end of the fluted channel 402 may be rounded to facilitate fluid flow into the fluted channel.

Figure 5:
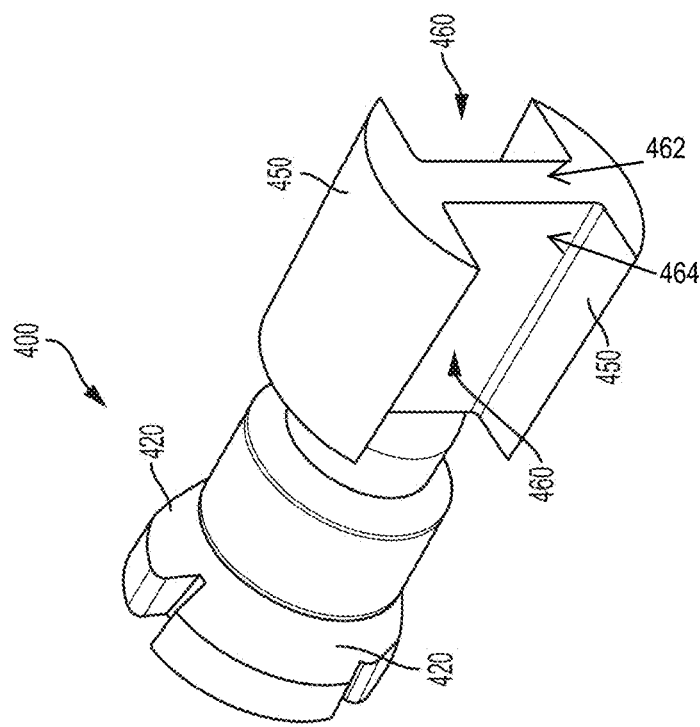

FIG. 5 shows an extended baffle 450 leading up to the break-up insert 400. As shown, the baffle 450 is designed to maintain two pre-cursor components separate from one another until they reach the break-up insert 400. The baffle includes a central inner wall 462 and an interrupted outer-wall 464. When more than two pre-cursor components are used, the baffle may provide additional structure to maintain the additional pre-cursor components separately. Upon reaching the break-up insert 400, as described above, the fluids flow around the break-up insert 400 in the channel formed between the break-up insert 400 and the nozzle housing wall 110. Due to the limited space in the channel, limited, if any, mixing occurs. What mixing does occur is essentially limited to the interface of the product flows, which is not efficient for curing purposes. This limited contact at this point also reduces the likelihood of clogging. The product flows are then directed toward the swirl chamber as described above.

Figure 7:
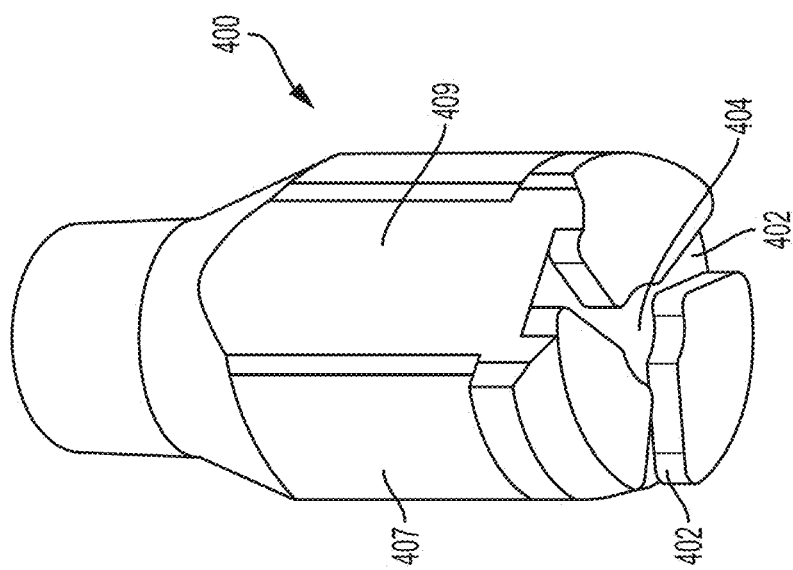
Figure 6:
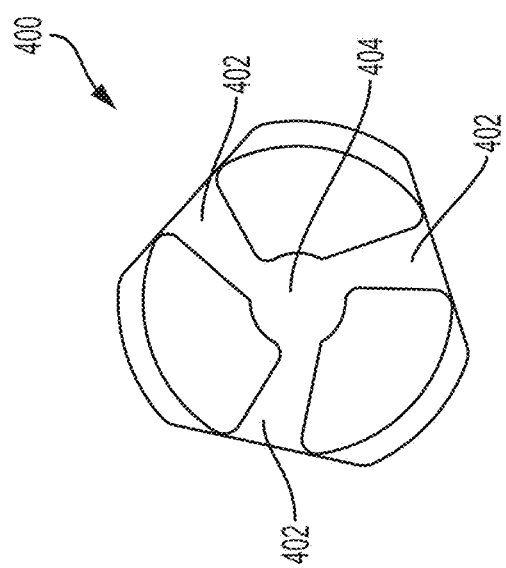

FIGS. 6 and 7 depict an alternative embodiment of the break-up tip 400. As can be seen from the distal end view of FIG. 6, the break-up tip is not round, but rather has a rounded triangular shape. This is illustrative of the point that the nozzle housing and the break-up insert may take any suitable shape, so long as the pre-cursor fluids are directed around the break-up insert to the fluted channels 402 in the distal end of the break-up insert. As seen in FIGS. 6 and 7, the sidewall of the break-up insert 400 has a rounded portion 407 and a flat portion 409. When placed in a nozzle housing having a cylindrical nozzle housing wall 110, a channel is formed therebetween allowing fluid to flow directly to one of the fluted channels. In some embodiments, the rounded portion 407 is in a close fitting arrangement with the nozzle housing wall 110, so as to substantially eliminate any fluid flow therebetween. As depicted in FIG. 6, the fluted channels 402 feed into the swirl chamber 404 at acute angles to induce a swirling motion. FIG. 7 shows a perspective view of an exemplary break-up insert.

Figure 9:
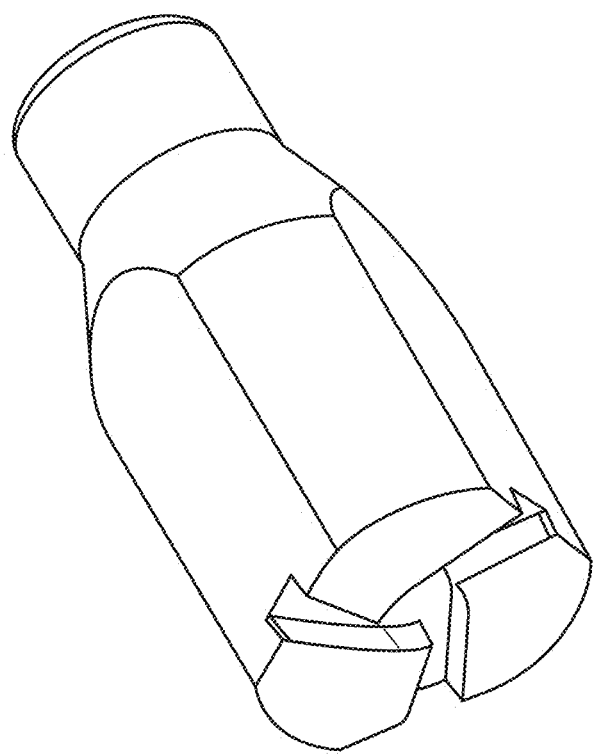
Figure 8:
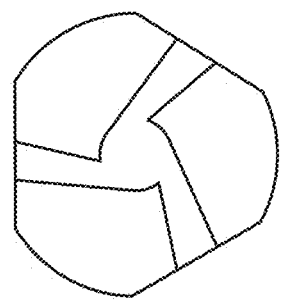

FIGS. 8 and 9 depict yet another alternative embodiment. This embodiment is similar to that of FIGS. 6 and 7. Notably, however, an exterior edge of each fluted channel is substantially tangential to the outer periphery of the swirl chamber. This defines an acute angle at which the fluid components enter the swirl chamber essentially driving the fluid in a spiral or swirl pattern around and into the swirl chamber causing mixing.

Figure 11:
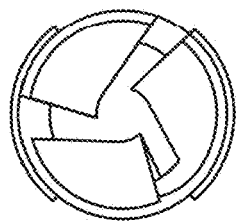
Figure 12:
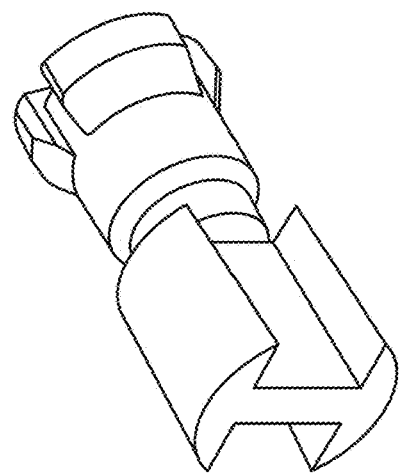
Figure 10:
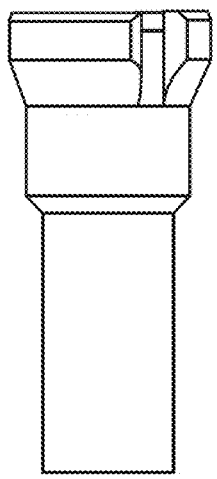

FIGS. 10, 11, and 12 depict yet another alternative embodiment. As shown, the break-up insert includes a baffle portion which is used to keep the pre-cursor fluids separate from each other until they reach the break-up tip. As illustrated, the I-like construction of the baffle provides separated conduits for each two components to flow. Any number of baffles can be used to create an appropriate number of conduits.

The swirl chamber design is not limited to use with multi-component syringes, but may be adapted for use with any multi-lumen delivery system. For example, some systems have a longer extended delivery tip including multiple delivery lumens. These require a different nozzle, one example being depicted in FIG. 5. The nozzle shape is adapted for proper coupling to the delivery lumen, but the principles of the nozzle are the same, with pre-cursor fluid being directed through a channel between the break-up insert and the housing wall, to and through a plurality of fluted channels to a swirl chamber in the distal end of the break-up insert and finally through a central exit orifice in the distal end of the housing. For example, a nozzle housing, a break-up insert, may be adapted for use with a three-lumen delivery device. Notably, the three lumen would feed into the channel defined by the nozzle housing and the break-up insert and flow into the swirl chamber via three fluted channels in the distal end of the break-up insert in a manner similar to the dual lumen system described above. In some embodiments, the nozzle tips are interchangeable between multiple delivery devices, regardless of the number of lumen. In other embodiments, particularly those employing a baffle, the nozzle tip is adapted specifically for the number of lumen and the number of pre-cursor components.

Although the embodiments disclosed and depicted herein employ a break-up insert that essentially blocks any fluid flow through its center, it is also contemplated that a dedicated lumen could pass through the center right to the swirl chamber for addition of another pre-cursor fluid but avoiding the other fluids entirely until at the swirl chamber. This could be used to apply a later addition of an additional component, to introduce a pulse of gas or solvent to dislodge a clogged tip or put to other use.

Any number of variations are possible in light of the disclosure herein. Nothing herein is meant to limit the possible combinations of numbers of lumen, number of fluted channels, or the size and shape of any of the relevant parts of the apparatus.

What is claimed is:

1. A nozzle tip assembly for mixing multiple pre-cursor fluids, the nozzle tip assembly comprising:
   a nozzle housing comprising
      a proximal end adapted for receiving a delivery portion of a multi-lumen dispenser having at least two lumen for separate delivery of each pre-cursor fluid,
      a distal end defining an exit orifice, and
      a sidewall extending from proximal end to distal end;
   a break-up insert comprising
      a break-up insert proximal end,
      a break-up insert distal end, further defining at least three fluted channels and a central, recessed swirl chamber and
      a sidewall extending between the break-up insert proximal end and the break-up insert distal end, wherein the sidewall of the break-up insert and the sidewall of the nozzle housing define a channel therebetween extending around the periphery of the break-up insert for fluid communication between the at least two lumen and the at least three fluted channels, wherein the distance between the sidewall of the break-up insert and the nozzle housing sidewall decreases in a direction from a proximal end to a distal end of the break-up insert; and a baffle extending from the proximal end of the break up insert, said baffle including a central inner wall preventing fluid passage therethrough and an interrupted outer wall along a length thereof, the interrupted outer wall and the sidewall of the nozzle housing cooperating to form at least two channels configured to maintain each pre-cursor fluid separate from each other as they approach the breakup insert.

2. The nozzle tip assembly of claim 1, wherein the swirl chamber is defined by a substantially centrally located semi-spherical recess in the distal end of the break-up insert.

3. The nozzle tip assembly of claim 1, wherein each of the fluted channels approaches the swirl chamber at an angle to facilitate mixing of the pre-cursor fluids in the swirl chamber.

4. The nozzle tip assembly of claim 1, wherein the break-up insert comprises one or more sloped shoulders to decrease the distance between the sidewall of the break-up insert and the nozzle housing sidewall.

5. The nozzle tip assembly of claim 1, wherein the at least three fluted channels are equidistant from one another.

6. The nozzle tip assembly of claim 1, wherein the nozzle housing is adapted for coupling to a dual barrel syringe.

7. The nozzle tip assembly of claim 1, wherein the nozzle housing is adapted for coupling to a dual lumen delivery device.

8. The nozzle tip assembly of claim 1, wherein the nozzle housing is adapted for coupling to a tri-lumen delivery device.

9. A multi-component delivery device comprising:
a multi-lumen delivery device;
a nozzle housing comprising
   a proximal end adapted for receiving a delivery portion of the multi-lumen delivery device having at least two lumen for respective, separate delivery of each pre-cursor fluid,
   a distal end defining an exit orifice, and
   a sidewall extending from proximal end to distal end;
a break-up insert comprising
   a break-up insert proximal end,
   a break-up insert distal end, further defining at least three fluted channels and a central, recessed swirl chamber and
   a sidewall extending between the break-up insert proximal end and break-up insert distal end, wherein the sidewall of the break-up insert and the sidewall of the nozzle housing define a channel therebetween for fluid communication between the lumen and the at least three fluted channels, wherein the distance between the sidewall of the break-up insert and the nozzle housing sidewall decreases in a direction from a proximal end to a distal end of the break-up insert;
wherein the nozzle housing is coupled to the multi-lumen delivery device such that each of the lumens is in fluid communication with a channel defined by a baffle extending between a distal end of the multi-lumen delivery device and the proximal end of the break up insert, which is in fluid communication with the swirl chamber and exit orifice via the at least three fluted channels and the channel between the nozzle housing and break-up insert sidewall, wherein the baffle includes a central inner wall preventing fluid passage therethrough and an interrupted outer wall along a length thereof, the interrupted outer wall and the sidewall of the nozzle housing cooperating to form the channel.

* * * * *